United States Patent
Dargis et al.

(10) Patent No.: US 11,138,697 B2
(45) Date of Patent: Oct. 5, 2021

(54) X-RAY IMAGING APPARATUS

(71) Applicant: Shimadzu Corporation, Kyoto (JP)

(72) Inventors: Michel Dargis, Laval (CA); Takanori Yoshida, Kyoto (JP); Keiichi Tanno, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 117 days.

(21) Appl. No.: 16/604,229

(22) PCT Filed: Apr. 9, 2018

(86) PCT No.: PCT/JP2018/014897
§ 371 (c)(1),
(2) Date: Oct. 10, 2019

(87) PCT Pub. No.: WO2018/190291
PCT Pub. Date: Oct. 18, 2018

(65) Prior Publication Data
US 2020/0151856 A1 May 14, 2020

(30) Foreign Application Priority Data
Apr. 13, 2017 (JP) .............................. JP2017-080076

(51) Int. Cl.
*G06K 9/00* (2006.01)
*G06T 5/00* (2006.01)
(Continued)

(52) U.S. Cl.
CPC ............... *G06T 5/003* (2013.01); *A61B 6/12* (2013.01); *A61B 6/5205* (2013.01);
(Continued)

(58) Field of Classification Search
CPC . G06T 5/003; G06T 5/50; G06T 11/60; G06T 2207/10116; G06T 2207/20201;
(Continued)

(56) References Cited

U.S. PATENT DOCUMENTS 7,415,169 B2   8/2008  Florent et al.
7,991,453 B2   8/2011  Florent et al.
(Continued)

FOREIGN PATENT DOCUMENTS

JP   2005510288 A   4/2005
JP   2006506117 A   2/2006
(Continued)

OTHER PUBLICATIONS

Written Opinion of the International Searching Authority for International Application PCT/JP2018/014897 dated May 29, 2018 with partial, machine, English translation.
(Continued)

*Primary Examiner* — Solomon G Bezuayehu
(74) *Attorney, Agent, or Firm* — Muir Patent Law, PLLC

(57) ABSTRACT

An image processor (13) of an X-ray imaging apparatus (100) is configured to be switchable to a full period image composition mode in which a composite image (M) is generated by superimposing images in an entirety of an image generation period and a partial period image composition mode in which the composite image is generated by superimposing the images in a part of the image generation period.

11 Claims, 6 Drawing Sheets

(51) Int. Cl.
*A61B 6/12* (2006.01)
*A61B 6/00* (2006.01)
*G06T 5/50* (2006.01)
*G06T 11/60* (2006.01)

(52) U.S. Cl.
CPC .............. *A61B 6/5235* (2013.01); *A61B 6/54* (2013.01); *G06T 5/50* (2013.01); *G06T 11/60* (2013.01); *G06T 2207/10116* (2013.01); *G06T 2207/20201* (2013.01); *G06T 2207/20221* (2013.01); *G06T 2207/30052* (2013.01)

(58) Field of Classification Search
CPC . G06T 2207/20221; G06T 2207/30052; G06T 11/008; G06T 2207/30021; G06T 3/0068; A61B 6/12; A61B 6/5205; A61B 6/5235; A61B 6/54; A61B 6/463; A61B 6/5264
See application file for complete search history.

(56) References Cited

U.S. PATENT DOCUMENTS

| | | | |
|---|---|---|---|
| 8,594,271 B2 | 11/2013 | Sakaguchi et al. | |
| 9,532,754 B2 | 1/2017 | Sakaguchi et al. | |
| 10,028,711 B2 | 7/2018 | Sakaguchi et al. | |
| 2003/0138149 A1* | 7/2003 | Iizuka .................. | H04N 9/8227 382/236 |
| 2007/0171286 A1* | 7/2007 | Ishii ....................... | H04N 5/272 348/239 |
| 2008/0043917 A1* | 2/2008 | Oreper .................. | G01V 5/005 378/116 |
| 2010/0034356 A1* | 2/2010 | Hayashida .............. | H04L 67/12 378/98 |
| 2010/0166337 A1* | 7/2010 | Murashita .............. | H04N 5/265 382/284 |
| 2011/0029326 A1* | 2/2011 | Venon .................... | G06Q 10/06 705/3 |
| 2014/0039303 A1* | 2/2014 | Kanzaki ................ | A61B 6/504 600/424 |
| 2014/0071324 A1* | 3/2014 | Tokunaga ........... | H04N 5/23229 348/333.02 |
| 2014/0316196 A1* | 10/2014 | Wichern .............. | A61B 1/0684 600/109 |
| 2015/0128096 A1* | 5/2015 | Rizvi .................... | G16H 30/20 715/863 |
| 2016/0095568 A1* | 4/2016 | Takanaka ............... | A61B 6/487 378/62 |
| 2016/0191158 A1* | 6/2016 | Aoyama .............. | H04B 10/116 398/172 |
| 2016/0269713 A1* | 9/2016 | Kasumi .............. | G02B 23/2484 |
| 2016/0338674 A1* | 11/2016 | Yamamoto ............... | A61B 8/14 |
| 2018/0280727 A1* | 10/2018 | Takahashi ........... | A61B 6/5205 |
| 2018/0317865 A1 | 11/2018 | Sakaguchi et al. | |

FOREIGN PATENT DOCUMENTS

| | | |
|---|---|---|
| JP | 2010131371 A | 6/2010 |
| JP | 2016131618 A | 7/2016 |

OTHER PUBLICATIONS

Notice of Reasons for Refusal dated Aug. 25, 2020 for corresponding Japanese Patent Application No. JP2018-056616, submitted with a machine translation.

\* cited by examiner

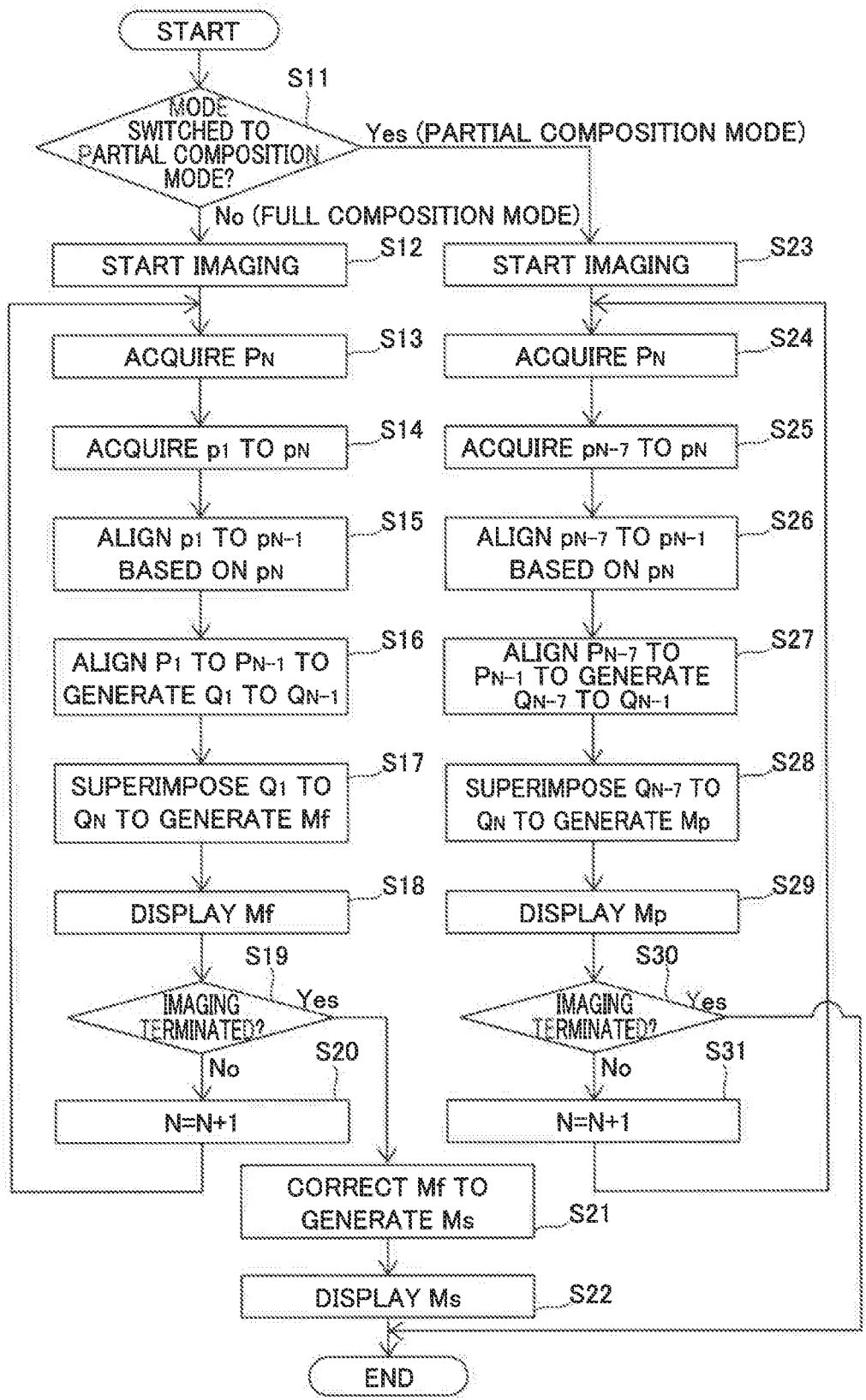

X-RAY IMAGING APPARATUS

TECHNICAL FIELD

The present invention relates to an X-ray imaging apparatus.

BACKGROUND ART

Conventionally, an X-ray imaging apparatus that generates a composite image by superimposing images based on radiation detection signals is known. Such an X-ray imaging apparatus is disclosed in Japanese Translation of PCT International Application Publication No. 2005-510288, for example.

Japanese Translation of PCT International Application Publication No. 2005-510288 discloses a medical viewing system used for endovascular interventional treatment using a balloon with a marker for alignment and a stent (device) attached to the balloon and less likely to absorb X-rays (radiation) than the marker. In the medical viewing system disclosed in Japanese Translation of PCT International Application Publication No. 2005-510288, a new image captured using X-rays is aligned with a marker of a reference image. A sequence image obtained by performing time integration on (superimposing) the aligned images is displayed on a display means.

In the endovascular interventional treatment using the medical viewing system disclosed in Japanese Translation of PCT International Application Publication No. 2005-510288, the balloon to which the stent is attached is placed at a stenotic portion of the blood vessel, and the balloon is inflated to place the stent at the stenotic portion. In the endovascular interventional treatment, a procedure may be performed while the sequence image is checked in a state in which the relative position of the balloon (markers) to the stent is substantially unchanged when the deployed state of the stent is checked, for example. Furthermore, in the endovascular interventional treatment, the procedure may also be performed while the sequence image is checked in a state in which there is a change in the relative position of the balloon (markers) to the stent when a new stent is aligned with the existing stent already deployed, for example.

PRIOR ART

Patent Document

Patent Document 1: Japanese Translation of PCT International Application Publication No. 2005-510288

SUMMARY OF THE INVENTION

Problem to be Solved by the Invention

However, in the medical viewing system disclosed in Japanese Translation of PCT International Application Publication No. 2005-510288, when the procedure is performed while the sequence image is checked in a state in which there is a change in the relative position of the balloon (markers) to the stent, the stent is blurred in the sequence image, and the visibility of the stent (device) is disadvantageously deteriorated in the sequence image (composite image). Specifically, when images having a large change in the position of the stent due to significantly different imaging time points are superimposed, for example, the stents are largely displaced from each other in the aligned images. Therefore, when the sequence image is generated by superimposing the images, the images are superimposed in a state in which the stents are largely displaced from each other in the sequence image, and thus the stent is blurred such that the visibility of the stent (device) is deteriorated.

The present invention is intended to solve the above problem. The present invention aims to provide an X-ray imaging apparatus capable of significantly reducing or preventing display of a composite image in which the visibility of a device is deteriorated on a display.

Means for Solving the Problems

An X-ray imaging apparatus according to an aspect of the present invention includes an image generator configured to generate an image based on a detection signal of radiation transmitted through a subject into which a device is introduced, an image processor configured to superimpose a plurality of images generated by the image generator, and a display configured to display the image. The image processor is configured to be switchable to a full period image composition mode in which a composite image is generated by superimposing the plurality of images in an entirety of an image generation period and a partial period image composition mode in which the composite image is generated by superimposing the plurality of images in a part of the image generation period.

In the X-ray imaging apparatus according to this aspect of the present invention, as described above, the image processor is configured to be switchable to the partial period image composition mode in which the composite image is generated by superimposing the images in a part of the image generation period. Accordingly, in the partial period image composition mode, the images to be superimposed are limited to the images within the partial period, and thus a change in the position of the device between the images to be superimposed can be reduced. Consequently, superimposition in a state in which the device is displaced can be significantly reduced or prevented, and thus blurring of the device in the composite image in which the images are superimposed can be significantly reduced or prevented. Therefore, display of the composite image in which the visibility of the device is deteriorated on the display can be significantly reduced or prevented.

Furthermore, in the X-ray imaging apparatus according to this aspect, as described above, the image processor is configured to be switchable to the full period image composition mode in which the composite image is generated by superimposing the images in the entirety of the image generation period and the partial period image composition mode in which the composite image is generated by superimposing the images in a part of the image generation period. Accordingly, when a procedure is performed in a state in which the position of the device is substantially unchanged over the entirety of the image generation period, the image processor is switched to the full period image composition mode such that the devices, the positions of which are substantially unchanged, are reliably superimposed, and thus the high-quality composite image in which the device is clear can be displayed on the display. On the other hand, when the position of the device is significantly changed in the image generation period, the image processor is switched to the partial period image composition mode such that display of the composite image in which the visibility of the device is deteriorated on the display can be significantly reduced or prevented, as described above. Consequently, the image processor is configured to be switchable to the full period image composition mode and the partial period image composition mode such that the composite image suitable for the procedure can be displayed on the display while display of the composite image in which the visibility of the device is deteriorated on the display is significantly reduced or prevented.

In the aforementioned X-ray imaging apparatus according to this aspect, the image processor is preferably configured to superimpose the plurality of images of a predetermined number of frames in the partial period image composition mode. According to this configuration, in the partial period image composition mode, the images to be superimposed are limited to the images of the predetermined number of frames within the partial period, and thus a change in the position of the device between the images to be superimposed can be reliably reduced. Consequently, superimposition in a state in which the device is displaced can be further significantly reduced or prevented, and thus blurring of the device in the composite image in which the images are superimposed can be further significantly reduced or prevented.

The aforementioned X-ray imaging apparatus according to this aspect preferably further includes a switching input for a user to switch the image processor to the full period image composition mode or the partial period image composition mode. According to this configuration, the user can switch the mode of the image processor to a mode that matches the procedure, and thus the composite image suitable for the procedure can be displayed on the display while display of the composite image in which the visibility of the device is deteriorated on the display is reliably significantly reduced or prevented.

In this case, the X-ray imaging apparatus preferably further includes a controller configured or programmed to perform control of acquiring information related to switching of the image processor to the full period image composition mode or the partial period image composition mode via the switching input when or before imaging is started. According to this configuration, the controller can acquire the information related to the mode when or before imaging is started, and thus the composite image can be generated by the image processor from the start of imaging in the switched mode. Consequently, for example, in a state in which the mode is switched to the full period image composition mode, the composite image in which the device is clear can be generated at an early stage, and thus the user can operate the X-ray imaging apparatus so as to stop radiation irradiation at an early stage. Therefore, an increase in the radiation exposure of the subject can be effectively significantly reduced or prevented.

In the aforementioned X-ray imaging apparatus according to this aspect, the device preferably includes a first device deployed inside the subject and a second device introduced into the subject separately from the first device and including a marker for alignment, and the image processor is preferably configured to superimpose the plurality of images of a predetermined number of frames so as to prevent blurring of the first device in the composite image due to movement of the second device relative to the first device in the partial period image composition mode. According to this configuration, in the partial period image composition mode, display of the composite image in which the visibility of the first device is deteriorated on the display can be significantly reduced or prevented.

In this case, the predetermined number of frames is preferably a number of frames that sufficiently enhances visibility of the second device in the composite image. According to this configuration, the composite image in which the second device is sufficiently visible and the deterioration of the visibility of the first device is significantly reduced or prevented can be displayed on the display.

In the aforementioned X-ray imaging apparatus according to this aspect, a number of frames of the plurality of images for generating the composite image at time of termination of imaging in the full period image composition mode is preferably larger than a number of frames of the plurality of images for generating the composite image in the partial period image composition mode. According to this configuration, the image processor can reliably generate the composite image in which the device is clear when imaging is terminated in the full period image composite mode.

In the aforementioned X-ray imaging apparatus according to this aspect, the image processor is preferably configured to generate a corrected composite image by correcting the composite image at time of termination of imaging to highlight the device in the full period image composite mode, and the display is preferably configured to display the corrected composite image when the imaging is terminated in the full period image composite mode. According to this configuration, the user can more accurately recognize the state of the device with the corrected composite image displayed on the display after imaging is terminated in the full period image composite mode.

In the aforementioned X-ray imaging apparatus according to this aspect, the image processor is preferably configured to superimpose all the plurality of images in the entirety of the image generation period in the full period image composition mode. According to this configuration, in the full period image composition mode, the composite image in which the device is clear can be generated at an earlier stage.

In the aforementioned configuration in which the plurality of images of the predetermined number of frames are superimposed in the partial period image composition mode, the image processor is preferably configured to superimpose the plurality of images of the predetermined number of latest frames in the partial period image composition mode. According to this configuration, in the partial period image composition mode, the latest composite image in which blurring of the device is significantly reduced or prevented can be displayed on the display, and thus the user can reliably perform the procedure while checking the latest composite image.

In the aforementioned X-ray imaging apparatus according to this aspect, the composite image is preferably a stent-highlighted image in which a stent as the device is highlighted. According to this configuration, display of the composite image in which the visibility of the stent is deteriorated on the display can be significantly reduced or prevented.

Effect of the Invention

According to the present invention, as described above, it is possible to significantly reduce or prevent display of the composite image in which the visibility of the device is deteriorated on the display.

BRIEF DESCRIPTION OF THE DRAWINGS

FIG. 14 is a diagram showing a control flow of the X-ray imaging apparatus according to the embodiment of the present invention.

MODES FOR CARRYING OUT THE INVENTION

An embodiment embodying the present invention is hereinafter described on the basis of the drawings.
(Configuration of X-Ray Imaging Apparatus)

The configuration of an X-ray imaging apparatus 100 according to the embodiment of the present invention is now described with reference to FIGS. 1 to 8.

Figure 1:
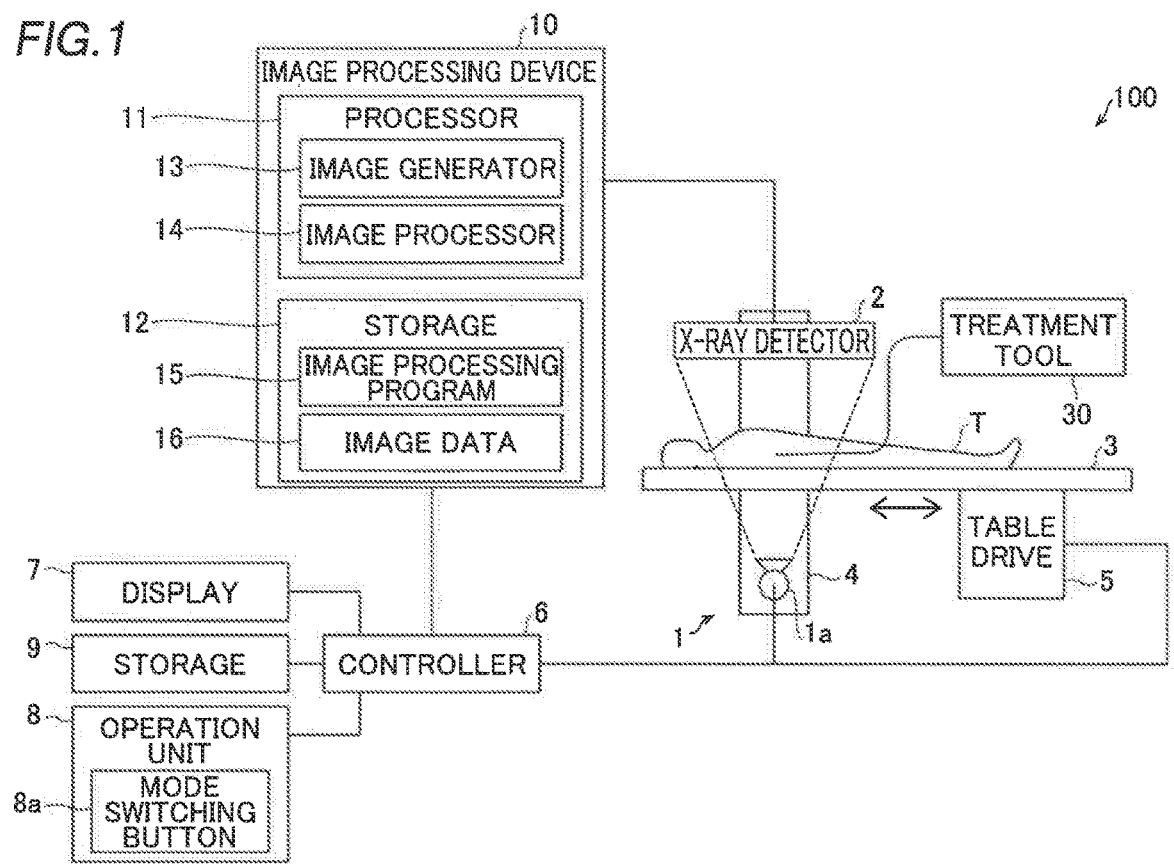
FIG. 1 is a block diagram showing the overall configuration of an X-ray imaging apparatus according to an embodiment of the present invention.

As shown in FIG. 1, the X-ray imaging apparatus 100 according to the embodiment of the present invention is an apparatus configured to capture an X-ray image obtained by imaging the inside of a subject T such as a human body by irradiating the subject T with X-rays (radiation) from the outside of the subject T.

The X-ray imaging apparatus 100 includes an X-ray irradiator 1, an X-ray detector 2, a controller 6, a display 7, an operation unit 8, a storage 9, and an image processing device 10.

The X-ray irradiator 1 irradiates the subject T into which a stent 31 (see FIG. 2) of a treatment tool 30 has been introduced with X-rays. The X-ray detector 2 detects the X-rays transmitted through the subject T. The X-ray irradiator 1 and the X-ray detector 2 face each other with a table 3, on which the subject T is placed, interposed therebetween. The X-ray irradiator 1 and the X-ray detector 2 are movably supported by a moving mechanism 4. The table 3 is horizontally movable by a table drive 5. The moving mechanism 4 and the table drive 5 are connected to the controller 6. The controller 6 is configured or programmed to move the X-ray irradiator 1, the X-ray detector 2, and the table 3 via the moving mechanism 4 and the table drive 5 such that a predetermined region of the subject T can be imaged as an image P (see FIG. 3).

The X-ray irradiator 1 includes an X-ray source 1a. The X-ray source 1a is an X-ray tube connected to a high voltage generator (not shown) and configured to generate X-rays when a high voltage is applied thereto. The X-ray source 1a is arranged in such a manner that the X-ray emission direction thereof faces a detection surface of the X-ray detector 2. The X-ray irradiator 1 is connected to the controller 6. The controller 6 is configured or programmed to control the X-ray irradiator 1 in accordance with preset imaging conditions such as a tube voltage, a tube current, and an X-ray irradiation time interval, and to generate X-rays from the X-ray source 1a.

The X-ray detector 2 is configured to detect the X-rays radiated from the X-ray irradiator 1 and transmitted through the subject T, and to output a detection signal corresponding to the detected X-ray intensity. The X-ray detector 2 is a flat panel detector (FPD), for example. The X-ray detector 2 is configured to output an X-ray detection signal having a predetermined resolution to the image processing device 10. The image processing device 10 is configured to acquire the X-ray detection signal from the X-ray detector 2, and to generate the image P (see FIG. 3).

The controller 6 is a computer including a central processing unit (CPU), a read only memory (ROM), a random access memory (RAM), etc. The controller 6 functions as a controller that controls each portion of the X-ray imaging apparatus 100 when the CPU executes a predetermined control program. The controller 6 is configured or programmed to control the X-ray irradiator 1 and the image processing device 10, and to drivingly control the moving mechanism 4 and the table drive 5, for example.

The display 7 is a monitor such as a liquid crystal display, and is configured to display the image P generated by the image processing device 10. The controller 6 is configured or programmed to control the display 7 to display the image P generated by the image processing device 10.

The operation unit 8 is configured to receive a user input related to X-ray imaging. The controller 6 is configured or programmed to receive an input operation from the user via the operation unit 8. The operation unit 8 includes a mode switching button 8a configured to enable switching of the mode of an image processor 14 described below. The mode of the image processor 14 is described below. The mode switching button 8a is an example of a "switching input" in the claims.

The storage 9 is a storage device such as a hard disk drive. The storage 9 is configured to store image data, imaging conditions, and various set values. Each of the display 7, the operation unit 8, and the storage 9 may be provided in the image processing device 10.

The X-ray imaging apparatus 100 is configured to acquire the image P by two types of methods of X-ray fluoroscopy and X-ray imaging. In the X-ray fluoroscopy, the subject T is irradiated with a smaller amount of radiation than in the X-ray imaging such that the radiation exposure of the subject T can be reduced, but a low-quality image P is acquired. On the other hand, in the X-ray imaging, an image P with a certain high quality is acquired.

The image processing device 10 is configured to perform image processing in real time while the image P is captured. The image processing device 10 is a computer including a processor 11 such as a CPU or a graphics processing unit (GPU) and a storage 12 such as a ROM and a RAM. That is, the image processing device 10 is configured to cause the processor 11 to execute an image processing program 15 stored in the storage 12. The image processing device 10 may be configured integrally with the controller 6 by causing the same hardware (CPU) as the controller 6 to execute the image processing program.

The storage 12 is configured to store the image processing program 15 for causing a computer to function as the image processing device 10. In addition, the storage 12 is configured to temporarily accumulate the image P generated by an image generator 13 described below, a composite image M, etc. as image data 16.

The image processing device 10 has the functions of the image generator 13 and the image processor 14 by executing the image processing program 15. The image generator 13 and the image processor 14 may be configured separately with dedicated processors.

The image generator 13 is configured to generate the image P based on detection signals of the X-rays transmitted through the subject T into which the stent 31 (see FIG. 2) of the treatment tool 30 has been introduced. The image generator 13 is configured to generate the image P in the form of a moving image based on the detection signals from the X-ray detector 2. That is, X-rays are intermittently radiated from the X-ray irradiator 1 to the subject T at predetermined time intervals, and the X-rays transmitted through the subject T are sequentially detected by the X-ray detector 2. The image generator 13 is configured to generate the image P at a frame rate of 15 fps by imaging the detection signals sequentially output from the X-ray detector 2. The frame rate may be about 7.5 fps to 30 fps. The image P is an image with pixel values of a predetermined number of gradations (such as 10 to 12 bits) in gray scale, for example. Therefore, a pixel with a low value is displayed with a low luminance value in black (darkly), and a pixel with a high value is displayed with a high luminance value in white (brightly). Note that the image may be inverted in black and white.

Figure 3:
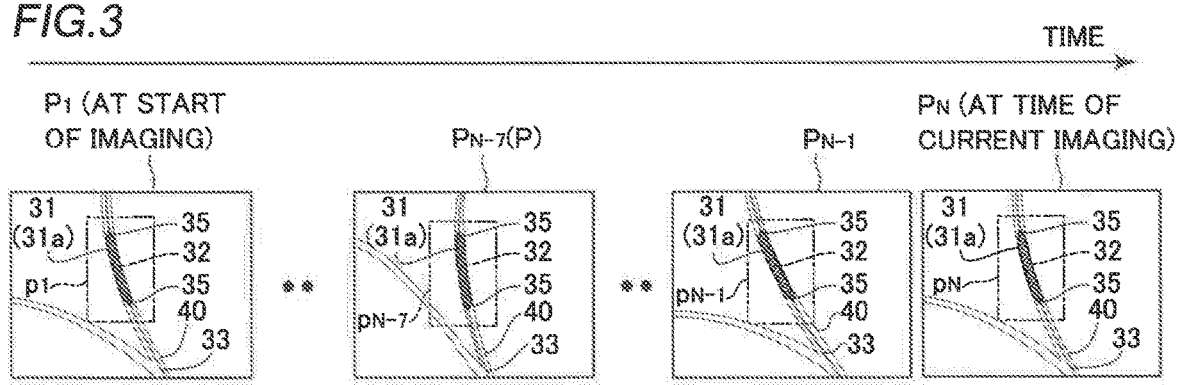
FIG. 3 is a diagram showing an example of images when a relative position between markers and the stent do not change.
Figure 4:
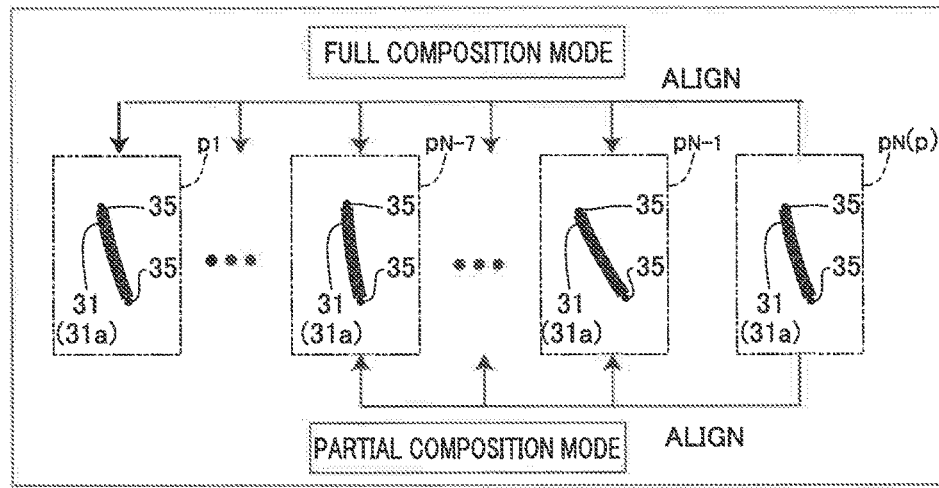
FIG. 4 is a diagram for illustrating alignment based on regions when the relative position does not change in the X-ray imaging apparatus according to the embodiment of the present invention.
Figure 5:
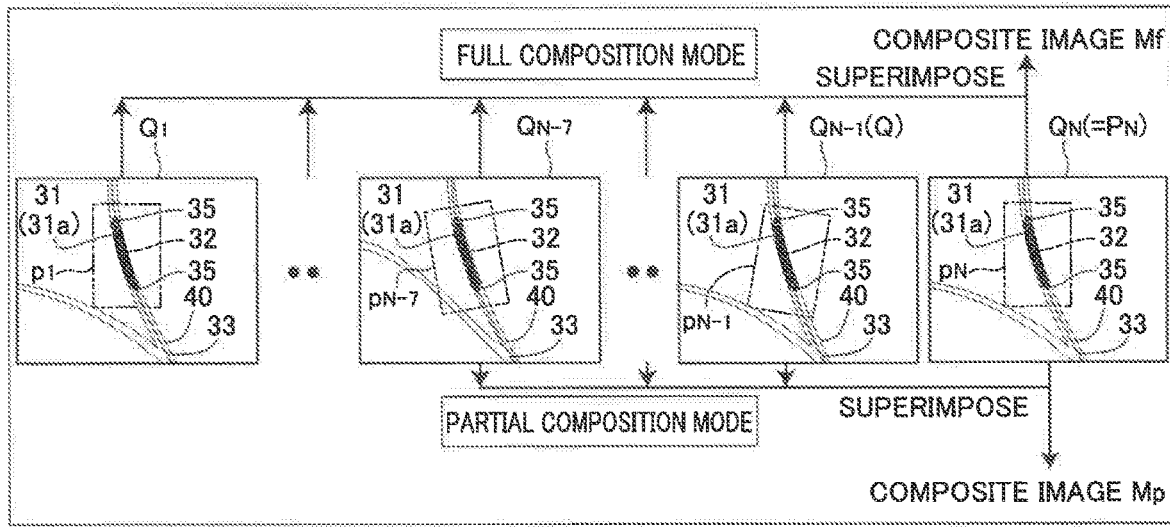
FIG. 5 is a diagram for illustrating superimposition of position-corrected images when the relative position does not change in the X-ray imaging apparatus according to the embodiment of the present invention.
Figure 6:
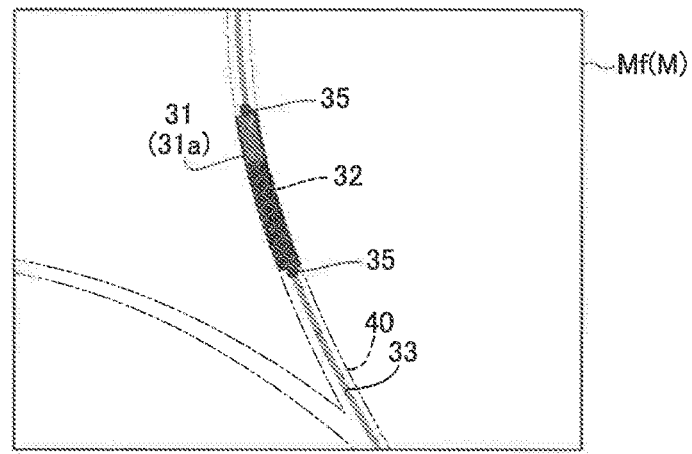
FIG. 6 is a diagram showing a composite image in a full composition mode when the relative position does not change in the X-ray imaging apparatus according to the embodiment of the present invention.
Figure 7:
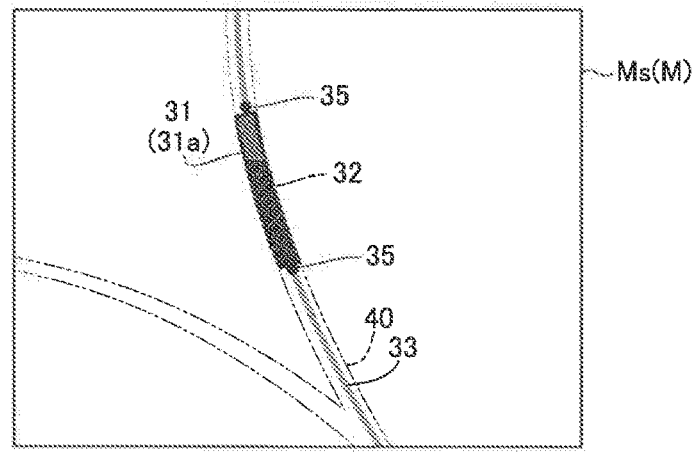
FIG. 7 is a diagram showing a corrected composite image in the full composition mode when the relative position does not change in the X-ray imaging apparatus according to the embodiment of the present invention.
Figure 8:
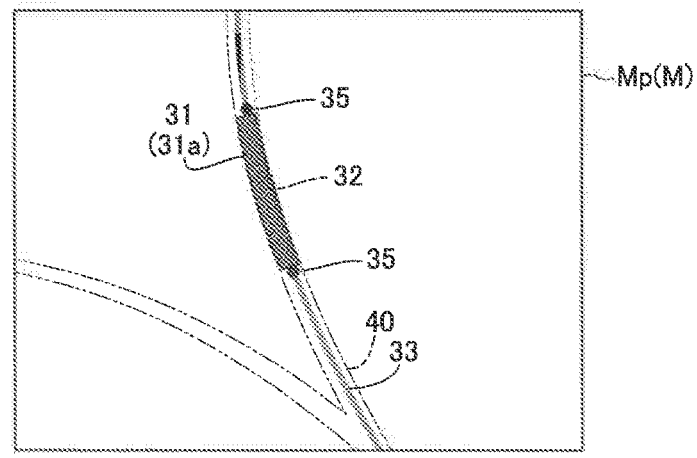
FIG. 8 is a diagram showing a composite image in a partial composition mode when the relative position does not change in the X-ray imaging apparatus according to the embodiment of the present invention.

The image processor 14 is configured to perform image processing for creating the composite image M (see FIGS. 6 to 8) by superimposing a plurality of images P (see FIG. 3) continuously generated by the image generator 13. Specifically, the image processor 14 first extracts regions p each including a pair of markers 35 from the plurality of images P for alignment, as shown in FIG. 3. Then, as shown in FIG. 4, the image processor 14 uses affine transformation, for example, to perform two-dimensional alignment such that the positions of the pair of markers 35 in each region p match the positions of the pair of markers 35 in a region $p_N$ of an image $P_N$ at the time of current imaging (latest). Then, as shown in FIG. 5, the image processor 14 generates position-corrected images Q after alignment by aligning the images P using the aligned regions p. Finally, the image processor 14 generates the composite (integrated) image M as a stent-highlighted image in which the stent 31 is highlighted by superimposing (performing time integration on) the position-corrected images Q, as shown in FIGS. 6 to 8.

The image processor 14 is configured to generate the composite image M every time an image P is newly generated by the image generator 13. Thus, the generated composite image M can be displayed as a moving image on the display 7 in real time.

In this embodiment, the image processor 14 is configured to switch a mode for creating the composite image M by superimposing the plurality of images P generated by the image generator 13 to either a full composition mode or a partial composition mode. In the full composition mode, the image processor 14 superimposes all the images P ($P_1$ to $P_N$; see FIG. 3) in the entirety of an image generation period to generate the composite image M (Mf (Ms); see FIG. 6 (FIG. 7)). In the partial composition mode, the image processor 14 superimposes images P ($P_{N-7}$ to $P_N$; see FIG. 6) of the latest (most recent) eight frames, which are a part of the image generation period, to generate the composite image M (Mp; see FIG. 8). In the partial composition mode, when the images of the eight frames are not obtained, the composite image M similar to that in the full composition mode is generated.

The "image generation period" refers to a period during which a plurality of images are generated by the image generator 13, and specifically refers to a period from the start of imaging to the time of current imaging. Furthermore, the term "superimpose images P of the latest eight frames" indicates that among the images P arranged in a time sequence, a new image $P_N$ and images P ($P_{N-7}$ to $P_{N-1}$) of seven frames in order from the new image $P_N$ toward the oldest, which are the images P of the eight frames, are superimposed. The full composition mode and the partial composition mode are examples of a "full period image composition mode" and a "partial period image composition mode" in the claims, respectively.

The controller 6 is configured or programmed to acquire information related to mode switching based on the operation contents of the mode switching button 8a when the user operates the mode switching button 8a. The controller 6 is configured or programmed to acquire the information related to mode switching in advance before the start of imaging. The controller 6 is also configured or programmed to switch the mode of the image processor 14 to either the full composition mode or the partial composition mode by transmitting the information related to mode switching to the image processor 14.

Examples of mode switching of the X-ray imaging apparatus 100 according to this embodiment in coronary (cardiovascular) intervention treatment are now described with reference to FIGS. 2 to 13.

The X-ray imaging apparatus 100 according to this embodiment can be used for coronary intervention treatment. The coronary intervention treatment is a treatment for dilating the stenosis of the blood vessel 40 (see FIG. 3) in the coronary artery of the heart.

Figure 2:
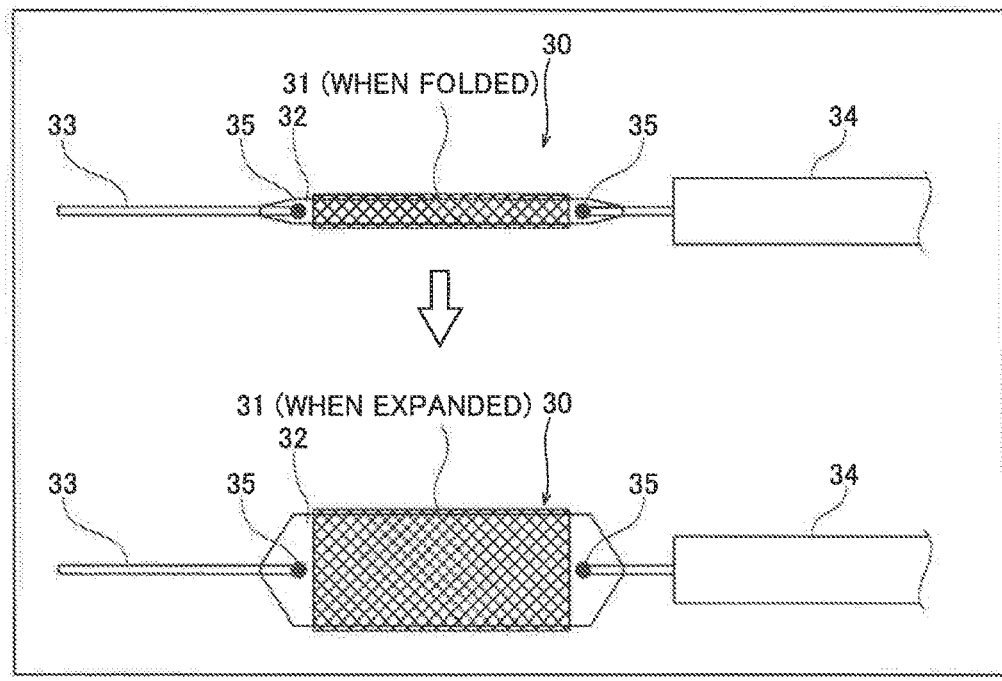
FIG. 2 is a diagram for illustrating a treatment tool including a stent.

In the coronary intervention treatment, as shown in FIG. 2, the treatment tool 30 including the stent 31 is used. The treatment tool 30 includes the stent 31, a balloon 32 to which the stent 31 is attached, a guide wire 33 to which the stent 31 and the balloon 32 are attached in the vicinity of the tip, and a catheter 34 in which the guide wire 33 is housed. The stent 31 has a cylindrical shape having a network structure made of thin metal or the like, is likely to transmit X-rays, and is unlikely to appear in the image P. Therefore, the balloon 32 to which the stent 31 is attached is provided with the pair of markers 35 made of a material having low X-ray permeability (or a radiopaque material) as marks. The pair of markers 35 are provided in the vicinity of opposite ends of the stent 31 so as to sandwich the stent 31. The stent 31 is configured to expand from a folded state when the balloon 32 is inflated. The stent 31 is an example of a "device" in the claims.

As specific treatment procedures of the coronary intervention treatment, first, a doctor inserts the catheter 34 into the blood vessel 40 of the subject T and moves the catheter 34 to a stenotic portion of the blood vessel 40 in the coronary artery of the heart via the blood vessel 40 while referring to a low-quality real-time moving image (image) captured by fluoroscopy and displayed on the display 7.

Then, the doctor positions the stent 31 (31a) and the balloon 32 at the stenotic portion while referring to a real-time moving image of the composite image M or a still image of the composite image M captured by the X-ray imaging and displayed on the display 7. Then, the doctor expands the stenotic portion of the blood vessel 40 by inflating the balloon 32, and expands the folded stent 31a so as to deploy it in the blood vessel 40. Thus, the blood vessel 40 is supported from the inside by the stent 31a. Furthermore, the doctor checks whether or not the stent 31a is correctly deployed while referring to the real-time moving image of the composite image M or the still image of the composite image M captured by the X-ray imaging. Then, when the stent 31a is not correctly deployed, the doctor adjusts the stent 31a by inflating the balloon 32 again, for example. When these procedures are performed, a relative position between the pair of markers 35 of the balloon 32 and the stent 31a is substantially unchanged.

The composite image M generated by the image processor 14 in each mode when the relative position between the markers 35 and the stent 31a does not change is now described.

(In Full Composition Mode)

When the mode is switched to the full composition mode, the image processor 14 first extracts regions p (regions $p_1$ to $p_N$) each including the pair of markers 35 from all of the plurality of images P (images $P_1$ to $P_N$) for alignment, as shown in FIG. 3. Then, as shown in FIG. 4, the image processor 14 aligns each of the regions $p_1$ to $p_N$. Thereafter, as shown in FIG. 5, the image processor 14 generates the position-corrected images $Q_1$ to $Q_{N-1}$ after alignment by aligning the images $P_1$ to $P_{N-1}$ using the aligned regions $p_1$ to $p_{N-1}$. Finally, the image processor 14 generates the composite image Mf shown in FIG. 6 by superimposing (performing time integration on) the position-corrected images $Q_1$ to $Q_N$ ($Q_N$ is equal to $P_N$).

The relative position between the markers 35 and the stent 31a does not change, and thus when alignment is performed such that the positions of the pair of markers 35 in each of the regions $p_1$ to $p_{N-1}$ match the positions of the pair of markers 35 in the region $p_N$, the position of the stent 31a in a position-corrected image $Q_i$ ($1 \leq i \leq N-1$) is substantially the same as that in the position-corrected image $Q_N$. Consequently, in the composite image Mf in which the position-corrected images Q (images P) are superimposed, the stent 31a is hardly displaced in the position-corrected images $Q_1$ to $Q_N$, and thus the stent 31a is highlighted on the display 7. Then, the composite image Mf is continuously generated and displayed as a real-time moving image on the display 7.

In the full composition mode, the number of images P (number of frames) for generating the composite image Mf increases as time elapses from the start of imaging, and thus in the composite image Mf displayed as a real-time moving image on the display 7, the stent 31a gradually becomes clear, and the image quality thereof is improved.

When the X-ray imaging in the full composition mode is terminated due to a sufficiently high-quality composite image Mf being obtained, the image processor 14 performs correction processing for highlighting the stent 31a on the last generated composite image Mf. In this correction processing, the stent 31a has a linear shape unlike the blood vessel 40, and thus the image processor 14 performs processing such as increasing the contrast of a linear portion, for example. Thus, the image processor 14 generates a corrected composite image Ms with higher quality in which the stent 31a is more highlighted from the composite image Mf. As shown in FIG. 8, the corrected composite image Ms is displayed as a still image on the display 7. Consequently, the doctor can reliably check whether or the stent 31a is correctly deployed.

The user can check in real time that the sufficiently high-quality composite image Mf has been obtained and terminate the X-ray imaging, and thus termination of the X-ray imaging with the composite image M having insufficient quality can be significantly reduced or prevented. In addition, the user can check in real time that the sufficiently high-quality composite image Mf has been obtained and quickly terminate the X-ray imaging, and thus an increase in the radiation exposure of the subject T can be effectively significantly reduced or prevented.

(In Partial Composition Mode)

On the other hand, when the mode is switched to the partial composition mode, the image processor 14 first extracts regions p (regions $p_{N-7}$ to $p_N$) each including the pair of markers 35 from the images P (images $P_{N-7}$ to $P_N$) of the latest (most recent) eight frames among the plurality of images P for alignment, as shown in FIG. 3. Then, as shown in FIG. 4, the image processor 14 aligns each of the regions $p_{N-7}$ to $p_N$. Then, as shown in FIG. 5, the image processor 14 generates the position-corrected images $Q_{N-7}$ to $Q_{N-1}$ after alignment by aligning the images $P_{N-7}$ to $P_{N-1}$ using the aligned regions $p_{N-7}$ to $p_{N-1}$. Finally, the image processor 14 generates the composite image Mp shown in FIG. 8 by superimposing the position-corrected images $Q_{N-7}$ to $Q_N$.

The relative position between the markers 35 and the stent 31a does not change, and thus the position of the stent 31a in a position-corrected image $Q_i$ ($N-7 \leq i \leq N-1$) is substantially the same as that in the position-corrected image $Q_N$, similarly to the full composition mode. Consequently, as shown in FIG. 7, in the composite image Mp in which the position-corrected images Q (images P) are superimposed, the stent 31a is hardly displaced in the position-corrected images $Q_{N-7}$ to $Q_N$, and thus the stent 31a is highlighted on the display 7. Then, the composite image Mp is continuously generated and displayed as a real-time moving image on the display 7.

In the partial composition mode, the number of images P (number of frames) for generating the composite image Mp is constantly eight even when time elapses from the start of imaging. Therefore, in the composite image Mp displayed as a real-time moving image, the sharpness of the stent 31a is substantially unchanged.

As general imaging conditions, when imaging is performed for three seconds at a frame rate of 15 fps, in the full composition mode, the composite image Mf is generated by combining images P (position-corrected images Q) of fourth-five frames at the end of imaging. That is, the number of frames (fourth-five frames) of the images for generating the composite image M at the time of termination of imaging in the full composition mode is larger than the number of frames (eight frames) in the partial composition mode. Consequently, when the relative position between the markers 35 and the stent 31a does not change, a higher-quality composite image M in which the stent 31a is clearer is displayed on the display 7 in the full composition mode than in the partial composition mode. Therefore, when the relative position between the markers 35 and the stent 31a does not change, it is preferable to switch the image processor 14 to the full composition mode rather than the partial composition mode.

On the other hand, when the stenotic portion is wide and one stent 31 (31a) cannot expand the entire stenotic portion, for example, the treatment tool 30 to which a new stent 31b (31) separate from the stent 31a deployed in the blood vessel 40 is attached is introduced into the stenotic portion of the blood vessel 40 in the coronary artery of the heart. Then, in order for a pair of stents 31a and 31b to reliably support the stenotic portion of the blood vessel 40 from the inside, the doctor positions the existing stent 31a already deployed, the new stent 31b, and the balloon 32 while referring to the real-time moving image of the composite image M captured by the X-ray imaging. The stents 31a and 31b are examples of a "first device" and a "second device" in the claims, respectively.

Figure 9:
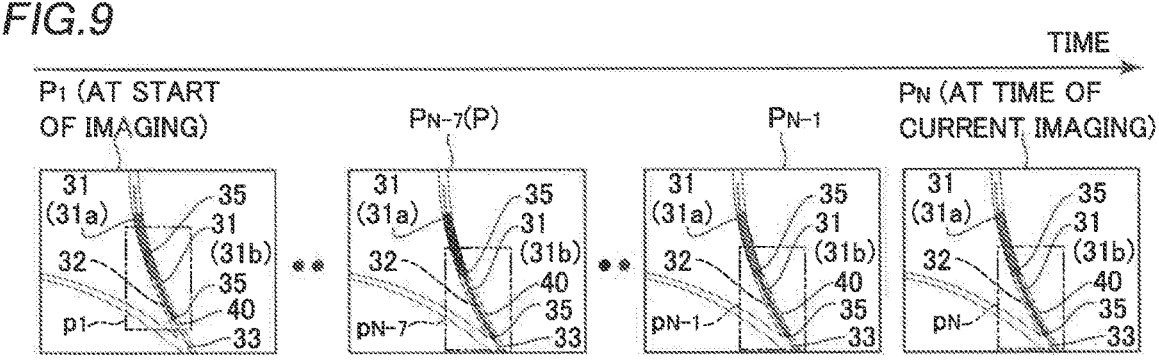
FIG. 9 is a diagram showing an example of images when the relative position between the markers and the stent changes.

Unlike the new stent 31b, the existing stent 31a is not attached to the balloon 32. Therefore, as shown in FIG. 9, a relative position between the pair of markers 35 of the balloon 32 and the new stent 31b does not change whereas the pair of markers 35 of the balloon 32 move relative to the existing stent 31a. That is, the relative position between the markers 35 and the existing stent 31a changes.

The composite image M generated by the image processor 14 in each mode when the relative position between the markers 35 and the stent 31a changes is now described.
(In Full Composition Mode)

Figure 10:
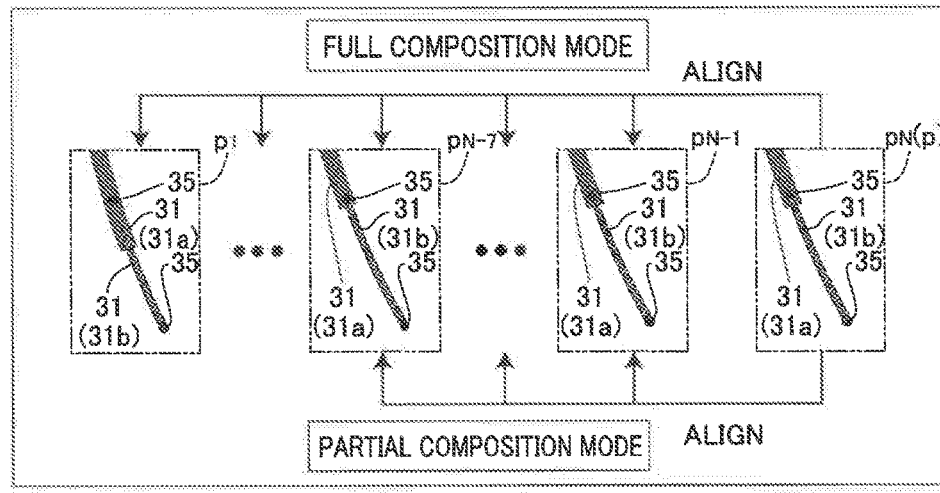
FIG. 10 is a diagram for illustrating alignment based on regions when the relative position changes in the X-ray imaging apparatus according to the embodiment of the present invention.
Figure 11:
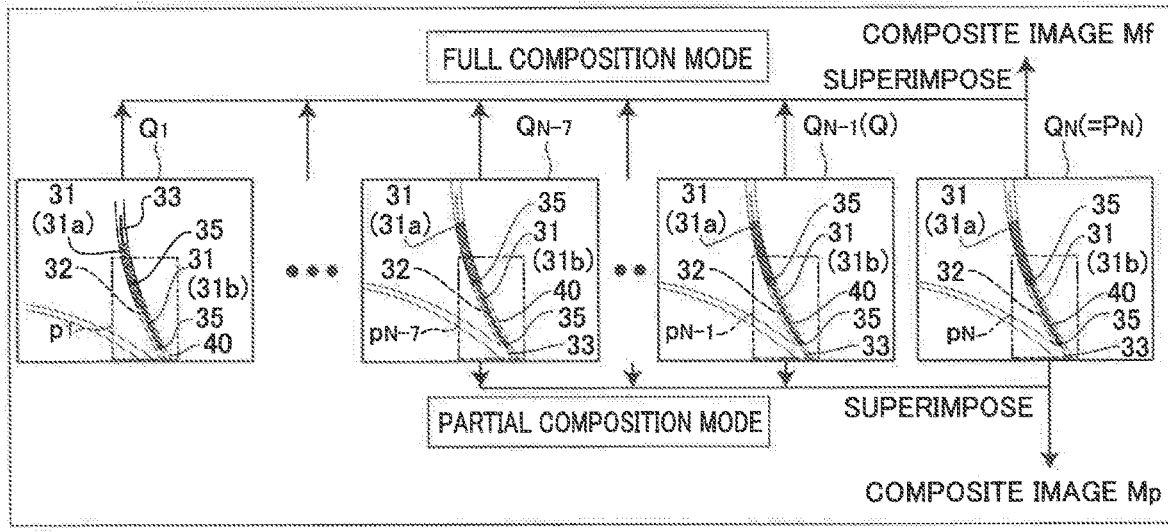
FIG. 11 is a diagram for illustrating superimposition of position-corrected images when the relative position changes in the X-ray imaging apparatus according to the embodiment of the present invention.

When the mode is switched to the full composition mode, the image processor 14 first extracts the regions p (regions $p_1$ to $p_N$) each including the pair of markers 35 from all of the plurality of images P (images $P_1$ to $P_N$), as shown in FIG. 9, similarly to the above case. Then, as shown in FIG. 10, the image processor 14 aligns the regions $p_1$ to $p_N$. Thereafter, as shown in FIG. 11, the image processor 14 generates the position-corrected images $Q_1$ to $Q_{N-1}$ using the regions $p_1$ to $p_{N-1}$. Finally, the image processor 14 generates the composite image Mf shown in FIG. 12 by superimposing the position-corrected images $Q_1$ to $Q_N$.

Figure 12:
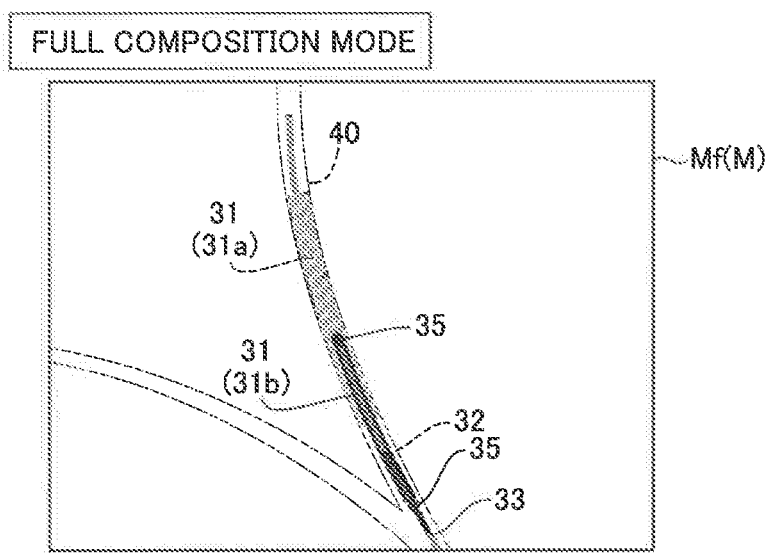
FIG. 12 is a diagram showing a composite image in the full composition mode when the relative position changes in the X-ray imaging apparatus according to the embodiment of the present invention.

The relative position between the pair of markers 35 of the balloon 32 and the existing stent 31a changes, and thus when alignment is performed such that the positions of the pair of markers 35 in each of the regions $p_1$ to $P_{N-1}$ match the positions of the pair of markers 35 in the region $p_N$, the position of the stent 31b in the position-corrected image $Q_i$ ($1 \leq i \leq N-1$) is substantially the same as that in the position-corrected image $Q_N$. Consequently, as shown in FIG. 12, in the composite image Mf in which the position-corrected images Q (images P) are superimposed, the stent 31b is highlighted. On the other hand, the existing stent 31a is positioned at different locations in the position-corrected image $Q_i$ and the position-corrected image $Q_N$ ($Q_1$ and $Q_N$ in FIG. 11, for example). Therefore, as shown in FIG. 12, in the composite image Mf in which the position-corrected images Q (images P) are superimposed, the stent 31a is blurred on the display 7 due to large displacement of the stent 31a in the position-corrected images $Q_1$ to $Q_N$.
(In Partial Composition Mode)

On the other hand, when the mode is switched to the partial composition mode, the image processor 14 first extracts the regions p (regions $p_{N-7}$ to $p_N$) each including the pair of markers 35 from the images P (images $P_{N-7}$ to $P_N$) of the latest eight frames among the plurality of images P, as shown in FIG. 9, similarly to the above case. Then, as shown in FIG. 10, the image processor 14 aligns the regions $p_{N-7}$ to $p_N$. Then, as shown in FIG. 11, the image processor 14 generates the position-corrected images $Q_{N-7}$ to $Q_{N-1}$ using the regions $p_{N-7}$ to $p_{N-1}$. Finally, the image processor 14 generates the composite image Mp shown in FIG. 13 by superimposing the position-corrected images $Q_{N-7}$ to $Q_N$.

Figure 13:
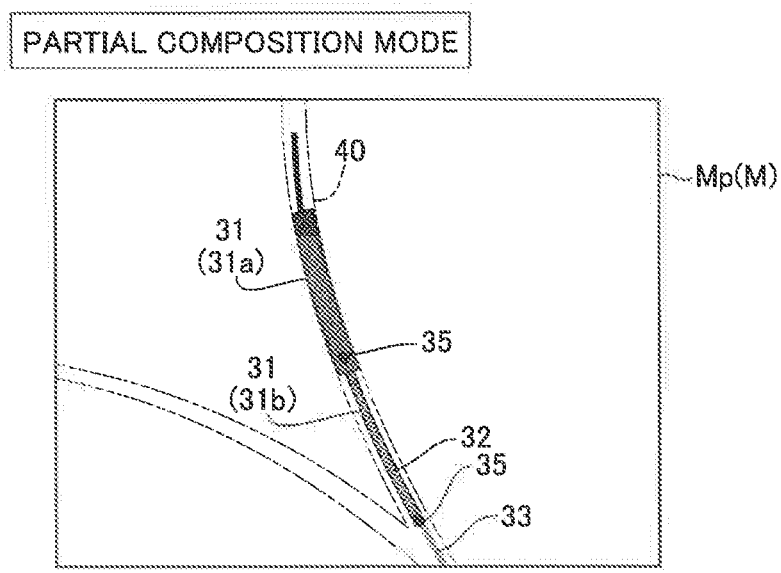
FIG. 13 is a diagram showing a composite image in the partial composition mode when the relative position changes in the X-ray imaging apparatus according to the embodiment of the present invention.

Although the relative position between the markers 35 and the stent 31a changes, the change in the relative position between the markers 35 and the stent 31a is small in the latest (most recent) eight frames (about 0.5 seconds). Thus, when alignment is performed such that the positions of the pair of markers 35 in each of the regions $p_{N-7}$ to $p_{N-1}$ match the positions of the pair of markers 35 in the region $p_N$, not only the position of the stent 31b but also the position of the existing stent 31a in the position-corrected image $Q_i$ ($N-7 \leq i \leq N-1$) is substantially the same as that in the position-corrected image $Q_N$. Consequently, as shown in FIG. 13, in the composite image Mp in which the position-corrected images Q (images P) are superimposed, the stents 31a and 31b are hardly displaced such that not only the stent 31b but also the existing stent 31a is highlighted on the display 7. In the partial composition mode, the number of frames is eight, and thus the number of frames that sufficiently enhances the visibility of the stent 31b is ensured.
(Comparison between Full Composition Mode and Partial Composition Mode)

Accordingly, in the X-ray imaging apparatus 100, when the user (such as a doctor) performs a procedure in which a relative position between the markers 35 and the stent 31 does not change, the user switches the mode of the image processor 14 to the full composition mode. Thus, the high-quality composite image Mf or the corrected composite image Ms in which the stent 31 is clearly highlighted can be displayed on the display 7 during and after the X-ray imaging. Furthermore, in the X-ray imaging apparatus 100, when the user performs a procedure in which the relative position between the markers 35 and the stent 31 changes, the user switches the mode of the image processor 14 to the partial composition mode. Thus, the composite image Mp in which the stent 31 is sufficiently highlighted without blurring can be displayed on the display 7 during the X-ray imaging.
(Control Flow)

A control flow of the X-ray imaging apparatus 100 is now described with reference to FIG. 14.

First, in step S11, the controller 6 determines whether or not the mode has been switched to the partial composition mode. When determining that the mode has been switched to the partial composition mode, the controller 6 advances to step S23 and performs X-ray imaging in step S23 to step S31 in a state in which the mode is switched to the partial composition mode.

When determining that the mode has not been switched to the partial composition mode, the controller 6 performs X-ray imaging in step S12 to step S22 in a state in which the mode has been switched to the full composition mode. Then, in step S12, when information related to an input operation for imaging start performed on the operation unit 8 by the user is transmitted to the controller 6, the controller 6 starts the X-ray imaging. In step S13, the controller 6 controls the X-ray irradiator 1 to radiate X-rays so as to cause the X-ray detector 2 to detect the X-rays transmitted through the subject T and output detection signals. Then, the image generator 13 generates an image $P_N$ based on the detection signals.

Thereafter, in step S14, the image processor 14 acquires regions $p_1$ to $p_N$ from images $P_1$ to $P_{N-1}$ generated prior to the image $P_N$ and the newly generated image $P_N$, respectively. In step S15, the image processor 14 aligns the regions $p_1$ to $p_{N-1}$ based on the region $p_N$. Thereafter, in step S16, the image processor 14 generates position-corrected images $Q_1$ to $Q_{N-1}$ by aligning the images $P_1$ to $P_{N-1}$ based on the results of alignment of the regions $p_1$ to $p_{N-1}$. In step S17, the image processor 14 generates a composite image Mf by superimposing the position-corrected images $Q_1$ to $Q_N$. Thereafter, in step S18, the composite image Mf generated by the image processor 14 is displayed on the display 7 via the controller 6.

In step S19, the controller 6 determines whether or not the X-ray imaging has been terminated when information related to an input operation for imaging termination performed on the operation unit 8 by the user is transmitted to the controller 6. When determining that the X-ray imaging has not been terminated, the controller 6 increments N (N=N+1) in step S20 and returns to step S13, and the image generator 13 generates a new image $P_N$.

When the controller 6 determines that the X-ray imaging has been terminated, in step S21, the image processor 14 generates a corrected composite image Ms by correcting the latest composite image Mf such that the stent 31 is highlighted. In step S22, the corrected composite image Ms generated by the image processor 14 is displayed on the display 7 via the controller 6. Thereafter, the controller 6 terminates the control flow.

When determining in step S11 that the mode has been switched to the partial composition mode, the controller 6 starts the X-ray imaging in step S23, similarly to step S12. In step S24, the image generator 13 generates an image $P_N$ based on the detection signals, similarly to step S12.

Thereafter, in step S25, the image processor 14 acquires regions $p_{N-7}$ to $p_N$ from the latest (most recent) images $P_{N-7}$ to $P_{N-1}$ and the newly generated image $P_N$ among images $P_1$ to $P_{N-1}$ generated prior to the image $P_N$, respectively. In step S26, the image processor 14 aligns the regions $p_{N-7}$ to $p_{N-1}$ based on the region $p_N$. Thereafter, in step S27, the image processor 14 generates position-corrected images $Q_{N-7}$ to $Q_{N-1}$ by aligning the images $P_{N-7}$ to $P_{N-1}$ based on the results of alignment of the regions $p_{N-7}$ to $p_{N-1}$. In step S28, the image processor 14 generates a composite image Mp by superimposing the position-corrected images $Q_{N-7}$ to $Q_N$. Thereafter, in step S29, the composite image Mp generated by the image processor 14 is displayed on the display 7 via the controller 6.

Then, in step S30, the controller 6 determines whether or not the X-ray imaging has been terminated, similarly to step S19. When determining that the X-ray imaging has not been terminated, the controller 6 increments N in step S31 and returns to step S24, and the image generator 13 generates a new image $P_N$. When determining that the X-ray imaging has been terminated, the controller 6 terminates the control flow.

Advantages of this Embodiment

According to this embodiment of the present invention, the following advantages are obtained.

According to this embodiment, as described above, the image processor 14 is configured to be switchable to the partial composition mode in which the composite image M (Mp) is generated by superimposing the images P in a part of the image generation period. Accordingly, in the partial composition mode, the images P to be superimposed are limited to the images P within the partial period (most recent), and thus a change in the position of the stent 31a (the relative position between the stent 31a and the pair of markers 35 of the balloon 32) between the images P to be superimposed can be reduced. Consequently, superimposition in a state in which the stent 31a is displaced can be significantly reduced or prevented, and thus blurring of the stent 31 in the composite image Mp in which the images P are superimposed can be significantly reduced or prevented. Therefore, display of the composite image Mp in which the visibility of the stent 31 is deteriorated on the display 7 can be significantly reduced or prevented.

According to this embodiment, the image processor 14 is configured to be switchable to the full composition mode in which the composite image Mf is generated by superimposing the images P in the entirety of the image generation period and the partial composition mode in which the composite image Mp is generated by superimposing the images P in a part of the image generation period. Accordingly, when the procedure is performed in a state in which the position of the stent 31 is substantially unchanged over the entirety of the image generation period, the image processor 14 is switched to the full composition mode such that the stents 31, the positions of which are substantially unchanged, are reliably superimposed, and thus the high-quality composite image Mf in which the stent 31 is clear can be displayed on the display 7. On the other hand, when the position of the stent 31 is significantly changed in the image generation period, the image processor 14 is switched to the partial composition mode such that display of the composite image Mp in which the visibility of the stent 31 is deteriorated on the display 7 can be significantly reduced or prevented. Consequently, the image processor 14 is configured to be switchable to the full composition mode and the partial composition mode such that the composite image M suitable for the procedure can be displayed on the display 7 while display of the composite image M in which the visibility of the stent 31 is deteriorated on the display 7 is significantly reduced or prevented.

According to this embodiment, the image processor 14 is configured to superimpose the images P of a predetermined number of frames (eight frames) in a part of the image generation period in the partial composition mode. Accordingly, in the partial composition mode, the images P to be superimposed are limited to the images P of the predetermined number of frames (8 frames) within the partial period, and thus a change in the position of the stent 31a between the images P to be superimposed can be reliably reduced. Consequently, superimposition in a state in which the stent 31a is displaced can be further significantly reduced or prevented, and thus blurring of the stent 31 in the composite image Mp in which the images P are superimposed can be further significantly reduced or prevented.

According to this embodiment, the X-ray imaging apparatus 100 includes the mode switching button 8a for the user to switch the image processor 14 to the full composition mode or the partial composition mode. Accordingly, the user can switch the mode of the image processor 14 to a mode that matches the procedure, and thus the composite image M suitable for the procedure can be displayed on the display 7 while display of the composite image M in which the visibility of the stent 31 is deteriorated on the display 7 is reliably significantly reduced or prevented.

According to this embodiment, the X-ray imaging apparatus 100 includes the controller 6 configured or programmed to perform control of acquiring the information related to switching of the image processor 14 to the full composition mode or the partial composition mode via the mode switching button 8a before the start of imaging. Accordingly, the controller 6 can acquire the information related to the mode before the start of imaging, and thus the composite image M can be generated by the image processor 14 from the start of imaging in the switched mode. Consequently, for example, in a state in which the mode is switched to the full composition mode, the composite image M in which the stent 31 is clear can be generated at an early stage, and thus the X-ray imaging apparatus 100 can be operated so as to stop radiation irradiation at an early stage. Therefore, an increase in the radiation exposure of the subject T can be effectively significantly reduced or prevented.

According to this embodiment, the image processor 14 is configured to superimpose the images of the predetermined number of frames (eight frames) so as to prevent blurring of the stent 31a in the composite image due to movement of the stent 31b relative to the stent 31a in the partial composition mode. Accordingly, in the partial composition mode, display of the composite image Mp in which the visibility of the stent 31a is deteriorated on the display 7 can be significantly reduced or prevented.

According to this embodiment, the predetermined number of frames (8 frames) in the partial composition mode is the number of frames that sufficiently enhances the visibility of the stent 31b in the composite image M. Accordingly, the composite image Mp in which the stent 31b is sufficiently visible and the deterioration of the visibility of the stent 31a is significantly reduced or prevented can be displayed on the display 7.

According to this embodiment, the number of frames of the images P for generating the composite image Mf at the time of termination of imaging in the full composition mode is larger than the number of frames (8 frames) of the images P for generating the composite image Mp in the partial composition mode. Accordingly, the image processor 14 can reliably generate the composite image Mf in which the stent 31 is clear at the end of imaging in the full composite mode.

According to this embodiment, the image processor 14 is configured to generate the corrected composite image Ms by correcting the composite image Mf at the time of termination of imaging to highlight the stent 31 in the full composite mode, and the display 7 is configured to display the corrected composite image Ms at the end of imaging in the full composite mode. Accordingly, the user can more accurately recognize the state of the stent 31 with the corrected composite image Ms displayed on the display 7 after imaging is terminated in the full composite mode.

According to this embodiment, the image processor 14 is configured to superimpose all the images P in the entirety of the image generation period in the full composition mode. Accordingly, in the full composition mode, the composite image Mf in which the stent 31 is clear can be generated at an earlier stage.

According to this embodiment, the image processor 14 is configured to superimpose the images P of the predetermined number of latest frames (eight frames) in the partial composition mode. Accordingly, in the partial composition mode, the latest composite image Mp in which blurring of the stent 31 is significantly reduced or prevented can be displayed on the display 7, and thus the user can reliably perform the procedure while checking the latest composite image Mp.

According to this embodiment, the composite image M is a stent-highlighted image in which the stent 31 is highlighted. Accordingly, display of the composite image M in which the visibility of the stent 31 is deteriorated on the display 7 can be significantly reduced or prevented.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the X-ray imaging apparatus 100 used for coronary (cardiovascular) intervention treatment has been shown as an example in the aforementioned embodiment, the present invention is not limited to this. The present invention may be applied to an X-ray imaging apparatus used for purposes other than coronary intervention treatment. The present invention capable of significantly reducing or preventing display of the composite image in which the visibility of the device is deteriorated due to a change in the position of the device relative to the markers on the display can also be used as an X-ray imaging apparatus used for endovascular interventional radiology (IVR) treatment in which the position of the device may be changed.

While the example in which the full composition mode (full period image composition mode) is a mode in which the composite image M (Mf) is generated by superimposing all the images P ($P_1$ to $P_N$) in the entirety of the image generation period has been shown in the aforementioned embodiment, the present invention is not limited to this. According to the present invention, in the full period image composition mode, only some of the images in the entirety of the image generation period may be used. For example, in the full period image composition mode, an image in which no marker can be detected among the images in the entirety of the image generation period may be excluded from the images to be superimposed. Alternatively, in the full period image composition mode, an image may be extracted every several frames from the images in the entirety of the period arranged in a time sequence, and images other than a plurality of extracted images may be excluded from the images to be superimposed. In the full period image composition mode, it is preferable to evenly extract images from the images in the entirety of the period arranged in a time sequence, and to superimpose the extracted images. Furthermore, the X-ray imaging apparatus may be configured such that in the full period image composition mode, a full composition mode in which all the images in the entirety of the image generation period are used, and a full period composition mode in which only some of the images in the entirety of the image generation period are used as described above can be selected.

While the example in which the partial composition mode (partial period image composition mode) is a mode in which the composite image M (Mp) is generated by superimposing the images P ($P_{N-7}$ to $P_N$) in a part of the image generation period has been shown in the aforementioned embodiment, the present invention is not limited to this. According to the present invention, even in the partial period image composition mode, only some of the images in a part of the image generation period may be used. For example, in the partial period image composition mode, an image in which no marker can be detected among the images in a part of the image generation period may be excluded from the images to be superimposed.

While the example in which the images P are aligned using the pair of markers 35 has been shown in the aforementioned embodiment, the present invention is not limited to this. According to the present invention, the images may be aligned without using the markers. For example, a plurality of feature points (portions of the subject that absorbs radiation more easily than other portions, for example) in the images may be detected, and the images may be aligned such that the plurality of feature points are matched between the images. In this case, the partial composition mode can be employed in order to significantly reduce or prevent generation of a composite image in which the stent is blurred due to movement of the feature points relative to the stent.

While the example in which the stent is used as the device has been shown in the aforementioned embodiment, the present invention is not limited to this. For example, the device may be a balloon without a stent attached thereto. Even in this case, when positioning of an existing stent and the balloon having markers is performed, for example, in order to significantly reduce or prevent generation of a composite image in which the stent is blurred due to a change in the position of the stent, the partial composition mode can be employed.

While the example in which in the partial composition mode (partial period image composition mode), the composite image M is generated by superimposing the images of the latest eight frames, which are a part of the image generation period, has been shown in the aforementioned embodiment, the present invention is not limited to this. According to the present invention, the number of frames in the partial period image composition mode is not limited to eight, but may be less than eight or more than eight. The number of frames is preferably changed according to the frame rate. For example, when the frame rate is 30 fps, images of fifteen frames more than eight frames may be superimposed, and when the frame rate is 7.5 fps, images of four frames less than eight frames may be superimposed. In the partial period image composition mode, when the number of frames of the images to be superimposed is too large (a period for acquiring frames becomes long), the device, the position of which is changed, tends to be blurred in the composite image, and when the number of frames of the images to be superimposed is too small, the device cannot be sufficiently highlighted in the composite image. Therefore, the number of frames of the images to be superimposed is preferably the number of frames corresponding to about 0.3 seconds to 1 second and four or more in the partial period image composition mode, but the present invention is not limited to this number of frames.

While the example in which in the partial composition mode (partial period image composition mode), the image processor 14 generates the composite image M by superimposing the images of the latest eight frames has been shown in the aforementioned embodiment, the present invention is not limited to this. According to the present invention, in the partial period image composition mode, the image processor may generate the composite image by superimposing images of a predetermined number of frames in a partial period other than the latest period. For example, the image processor may superimpose images of a predetermined number of frames in the first half or middle of the image generation period in the partial period image composition mode.

While the example in which the controller 6 acquires the information related to mode switching in advance before imaging starts has been shown in the aforementioned embodiment, the present invention is not limited to this. According to the present invention, the controller may be configured or programmed to acquire the information related to mode switching at the start of imaging. For example, the X-ray imaging apparatus may be configured to start imaging in the switched mode based on a switching operation on the switching input by the user. Alternatively, the X-ray imaging apparatus may be configured such that the mode of the image processor can be switched during X-ray imaging.

While the example in which when the user operates the mode switching button 8a, the mode of the image processor 14 is switched to either the full composition mode or the partial composition mode has been shown in the aforementioned embodiment, the present invention is not limited to this. According to the present invention, the mode of the image processor may be switched based on a switching instruction from the user by a method other than the operation of the mode switching button. For example, the mode of the image processor may be switched based on the user's voice, or the mode of the image processor may be switched based on the user's movement (the user's movement that blocks light of an optical sensor, for example).

Alternatively, the X-ray imaging apparatus may automatically switch the mode of the image processor without being based on a switching instruction from the user. At this time, the X-ray imaging apparatus may perform image recognition on the first image captured at the start of imaging, and may automatically switch the mode of the image processor based on the result of image recognition. For example, the X-ray imaging apparatus may be configured to automatically switch the mode of the image processor to the partial composition mode when a plurality of stents are recognized in the first image captured at the start of imaging, and to automatically switch the mode of the image processor to the full composition mode when a plurality of stents are not recognized in the first image captured at the start of imaging.

While the example in which the mode of the image processor 14 is switchable during X-ray imaging has been shown in the aforementioned embodiment, the present invention is not limited to this. According to the present invention, the mode of the image processor may be switchable during X-ray fluoroscopy.

While the example in which the regions p each including the pair of markers 35 are extracted and the images P are aligned has been shown in the aforementioned embodiment, the present invention is not limited to this. According to the present invention, the images may be aligned without extracting the regions.

DESCRIPTION OF REFERENCE NUMERALS

6: controller
7: display
8a: mode switching button (switching input)
13: image generator
14: image processor
31: stent (device)
31a: stent (device, first device)
31b: stent (device, second device)
100: X-ray imaging apparatus
M, Mf, Mp: composite image
Ms: corrected composite image
P: image
T: subject

The invention claimed is:

1. An X-ray imaging apparatus comprising:
an image generator configured to generate an image based on a detection signal of radiation transmitted through a subject into which a device is introduced;
an image processor configured to superimpose a plurality of images generated by the image generator; and
a display configured to display the image; wherein
the image processor is configured to be switchable to a full period image composition mode in which a composite image is generated by superimposing the plurality of images in an entirety of an image generation period and a partial period image composition mode in which the composite image is generated by superimposing the plurality of images in a part of the image generation period.

2. The X-ray imaging apparatus according to claim 1, wherein the image processor is configured to superimpose the plurality of images of a predetermined number of frames in the partial period image composition mode.

3. The X-ray imaging apparatus according to claim 1, further comprising a switching input for a user to switch the image processor to the full period image composition mode or the partial period image composition mode.

4. The X-ray imaging apparatus according to claim 3, further comprising a controller configured or programmed to perform control of acquiring information related to switching of the image processor to the full period image composition mode or the partial period image composition mode via the switching input when or before imaging is started.

5. The X-ray imaging apparatus according to claim 1, wherein
the device includes a first device deployed inside the subject and a second device introduced into the subject separately from the first device; and
the image processor is configured to superimpose the plurality of images of a predetermined number of frames so as to prevent blurring of the first device in the composite image due to movement of the second device relative to the first device in the partial period image composition mode.

6. The X-ray imaging apparatus according to claim 5, wherein the predetermined number of frames is a number of frames that sufficiently enhances visibility of the second device in the composite image.

7. The X-ray imaging apparatus according to claim 1, wherein a number of frames of the plurality of images for generating the composite image at time of termination of imaging in the full period image composition mode is larger than a number of frames of the plurality of images for generating the composite image in the partial period image composition mode.

8. The X-ray imaging apparatus according to claim 1, wherein
the image processor is configured to generate a corrected composite image by correcting the composite image at time of termination of imaging to highlight the device in the full period image composite mode; and
the display is configured to display the corrected composite image when the imaging is terminated in the full period image composite mode.

9. The X-ray imaging apparatus according to claim 1, wherein the image processor is configured to superimpose all the plurality of images in the entirety of the image generation period in the full period image composition mode.

10. The X-ray imaging apparatus according to claim 2, wherein the image processor is configured to superimpose the plurality of images of the predetermined number of latest frames in the partial period image composition mode.

11. The X-ray imaging apparatus according to claim 1, wherein the composite image is a stent-highlighted image in which a stent as the device is highlighted.

* * * * *